US00PP17776P2

(12) United States Plant Patent
Bradford

(10) Patent No.: US PP17,776 P2
(45) Date of Patent: May 29, 2007

(54) PEACH TREE NAMED 'CRIMSON PRINCESS'

(50) Latin Name: *Prunus persica*
Varietal Denomination: CRIMSON PRINCESS

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/311,235

(22) Filed: Dec. 20, 2005

(51) Int. Cl.
*A01H 5/00* (2006.01)

(52) U.S. Cl. ..... Plt./197
(58) Field of Classification Search ..... Plt./197
See application file for complete search history.

(56) References Cited

U.S. PATENT DOCUMENTS

| | | | | |
|---|---|---|---|---|
| PP7,918 P | | 7/1992 | Bradford | |
| PP7,953 P | | 8/1992 | Bradford | |
| PP11,631 P | * | 11/2000 | Fear et al. | Plt./197 |
| PP13,177 P2 | * | 11/2002 | Mowrey et al. | Plt./197 |

* cited by examiner

*Primary Examiner*—Wendy Haas

(57) ABSTRACT

The present invention relates to a peach tree, *Prunus persica,* and more particularly to a new and distinct variety characterized by a medium size, vigorous, hardy, self-fertile, productive and regular bearing tree. The fruit matures under the ecological conditions described in early June, with first picking on Jun. 1, 2005. The fruit is large in size, sweet and acidic in flavor, globose with some tipping on the apex in shape, clingstone in type, yellow in flesh color, full red in skin color, and firm but melting in texture. The variety was developed as a first generation cross using 'Ruby Diamond' nectarine as the selected seed parent and 'Crimson Lady' peach as the selected pollen parent.

1 Drawing Sheet

Botanical classification: *Prunus persica.*
Variety denomination: 'CRIMSON PRINCESS'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peak tree, which has been denominated varietally as 'CRIMSON PRINCESS'. The present variety was hybridized by me in 1996, grown as a seedling on its own root in my greenhouse, and transplanted to a cultivated area of my experimental orchard near Le Grand, Calif. in Merced County (San Joaquin Valley).

The variety was developed as a first generation cross using 'Ruby Diamond' (U.S. Plant Pat. No. 7,918) nectarine as the selected seed parent and 'Crimson Lady' (U.S. Plant Pat. No. 7,953) peach as the selected pollen parent. A single tree from the stated cross was selected as the claimed variety. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is substantially distinguished from its selected seed parent, 'Ruby Diamond' (U.S. Plant Pat. No. 7,918) nectarine, by producing clingstone peaches instead of freestone nectarines and by maturing about one month earlier.

The present variety is similar to its selected pollen parent, 'Crimson Lady' (U.S. Plant Pat. No. 7,953) peach, by producing fruit that is clingstone in type, mostly red in skin color, and yellow in flesh color, but is distinguished therefrom by requiring less chilling hours and by producing fruit that is larger in size, melting instead of in non-melting in texture, and that matures about five days later.

SUMMARY OF VARIETY

In summary, the present variety is characterized by a medium size, vigorous, hardy, self-fertile, productive and regular bearing tree. The fruit matures under the ecological conditions described in early June, with first picking on Jun. 1, 2005. The fruit is very large in size, sweet and acidic in flavor, globose with some tipping on the apex in shape, clingstone in type, yellow in flesh color, full red in skin color, and extremely firm and non-melting in texture.

DRAWING

The accompanying photograph exhibits four whole fruits positioned to display the characteristics of the skin color and form, one fruit divided transversely to the suture plane to reveal the flesh and stone, two mature leaves, a typical tip shoot, and a blossom in full bloom in the lower inset.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 4, 2005, on the original tree during its ninth growing season. All major color code designations are by reference to the Inter-Society Color Council, National Bureau of Standards. Common color names are also used occasionally.

Tree

Size: Medium, reaching a height of 10' [3.1 m.] and a spread of 9' [2.7 m.] after nine growing seasons utilizing typical dormant pruning.

Vigor: Vigorous, responding typically to irrigation and fertilization. The variety grows about 3' [0.9 m.] of surplus top-growth during the spring and summer. The plant should be grown on a standard commercial rootstock for production purposes.
Growth: Upright and dense.
Form: Trained to be base formed by pruning.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Approximate chilling requirement: 600 hours.
Trunk:
*Size.*—Medium, with a maximum diameter of 5⅛" [130 mm.] after the ninth growing season.
*Texture.*—Shaggy.
*Bark color.*—Dark grayish brown [62. d.gy.Br].
*Lenticels.*—Approximate Number Per Square Inch: 10. Color: Dark orange yellow [72. d.OY]. Average Size: 3/16" [4.8 mm.] to 7/16" [11.1 mm.]. Shape: Eye-shaped to elongated.
Branches:
*Size.*—Diameter of limb is 2¾" [69.9 mm.] measured 12" above the crotch and 2⅛" [54.0 mm.] measured 12" above the first fork.
*Texture.*—Rough, increasing to shaggy with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Approximate Number Per Square Inch: 50. Color: Moderate orange yellow [71. m.OY]. Typical size: 1/16" [1.6 mm.] to 3/16" [4.8 mm.]. Shape: Eye-shaped to elongated.
Leaves:
*Size.*—Medium. Average Length: 6" [152 mm.]. Average width: 1⅜" [35 mm.].
*Arrangement.*—Alternate.
*Thickness.*—Medium.
*Form.*—Elliptical.
*Apex.*—Acuminate.
*Base.*—Acute with a base angle of 60 to 85 degrees.
*Surface.*—Smooth.
*Color.*—Dorsal Surface: Moderate olive green [125. m.OlG]. Ventral Surface: Deep yellow green [118. deep YG].
*Margin.*—Finely serrate.
*Venation.*—Pinnately net veined.
*Petiole.*—Average Length: ⅜" [9.5 mm.]. Average Thickness: 1/16" [1.6 mm.]. Color: Strong yellow green [117. s.YG].
*Stipules.*—Number: 2 to 6 per growing tip. Average Length: ¼" [6.4 mm.]. Color: Strong yellow green [117. s.YG] becoming Strong yellowish brown [74. s.yBr] with age.
*Glands.*—Number: Mostly 2. Position: Alternate on the petiole and base of leaf blade. Size: Small. Form: Globose. Color: Strong yellow green [117. s.YG] becoming Strong yellowish brown [74. s.yBr] with age.
*Leaf buds.*—Medium, pointed.

Flower buds:
*Hardiness.*—Hardy, with respect to central California winters.
*Diameter.*—Typically 5/16" [7.9 mm.] 1 week before bloom.
*Length.*—Typically ½" [12.7 mm.] 1 week before bloom.
*Form.*—Not appressed.
*Surface.*—Pubescent.
*Color.*—Deep purplish pink [248. deep pPk].
Flowers: Perfect, complete, perigynous, usually a single pistil, typically thirty or more stamens, five sepals and petal locations alternately positioned.
*Type.*—Showy, large.
*Average flower diameter.*—1¾" [44.5 mm.].
*Number of petals.*—Usually five, with extra petal fragments rarely observed.
*Petal shape.*—Circular to oval.
*Petal margin.*—Somewhat wavy.
*Average petal diameter.*—11/16" [17.5 mm.].
*Average petal length.*—¾" [19.1 mm.].
*Petal apex.*—Rounded.
*Petal base.*—Rounded.
*Petal color.*—Pale pink [7. p.Pk] toward the apex, Light purplish pink [249. l.pPk] toward the base.
*Anther color.*—Strong reddish orange [35. s.rO] over Light yellow [86. l.Y] centers at bloom onset.
*Stigma color.*—Light greenish yellow [101. l.gY].
*Sepal color.*—Dark purplish red [259. d.pR].
*Sepal length.*—¼" [6 mm.].
*Sepal width.*—3/16" [5 mm.].
*Average pistil length.*—11/16" [17.5 mm.].
*Average stamen length.*—⅝" [15.9 mm.].
*Fragrance.*—Moderate.
*Blooming period.*—Medium compared with other varieties.
*Onset of bloom.*—One percent on Feb. 19, 2005.
*Date of full bloom.*—Feb. 27, 2005.
*Duration of bloom.*—One to two weeks, dependent on ambient temperature.
*Number per cluster.*—1 to 3 with single flowers most common.

FRUIT

Maturity when described: Firm ripe, Jun. 4, 2005.
Date of first picking: Jun. 1, 2005, noting that in 2005 fruit matured about two weeks earlier than normal.
Date of last picking: Jun. 10, 2005.
Size: Mostly uniform, large.
*Average diameter axially.*—3" [76.2 mm.].
*Average diameter across suture plane.*—3 1/16" [77.8 mm.].
*Typical weight.*—8.9 ounces [252 grams].
Form: Uniform, globose, and symmetrical.
*Longitudinal section form.*—Slightly obovate.
*Axial view.*—Round.
Suture: A distinct line located in a sharp groove near the base, a shallow groove along the sides, and a moderate groove toward the apex discontinuing 1" [25.4 mm.] past the pistil point.
Ventral surface: Rounded, lipped toward apex on both sides.
Lips: Slightly unequal.
Cavity: Flaring, elongated in the suture plane, suture showing on both sides, Brilliant yellow [83. brill.Y] stem markings typical.
*Depth.*—9/16" [14.3 mm.].
*Breadth.*—1¼" [31.8 mm.].

Base: Truncate, but slightly cordate if viewed parallel to the suture.
Apex: Rounded.
Pistil point: Mostly apical, short, slightly mammiform, slight depression on both sides.
Stem: Medium.
*Average length.*—7/16" [11.1 mm.].
*Average width.*—3/16" [4.8 mm.].
Skin:
*Thickness.*—Medium.
*Surface.*—Medium.
*Tenacity.*—Tenacious to flesh.
*Astringency.*—Slightly astringent.
*Tendency of crack.*—None observed.
*Color.*—Dark red [16. d.R] over a background of Dark yellowish pink [30. d.yPk].
Down: Moderate, short in length, does not roll up when rubbed.
Flesh:
*Color.*—Brilliant Yellow [83. brill.Y] with Moderate red [15. m.R] flecking one half way from stone to skin only on the ripest fruits.
*Surface of pit cavity.*—Clingstone with Light yellow [86. l.Y] broken fibers when twisted away from the stone.
*Amygdalin.*—Moderate.
*Juice.*—Abundant, rich.
*Texture.*—Firm, tough and melting.
*Fibers.*—Abundant, fine and tender.
*Ripens.*—Slightly earliest at the apex.
*Flavor.*—Acidic and sweet, averaging 12 brix.
*Aroma.*—Moderate.
*Eating quality.*—Good.

STONE

Type: Clingstone.
Form: Oval.
Hilum: Narrow, oblong.
Base: Slightly oblique.
Apex: Somewhat acuminate with an average tip length of 3/16" [4.8 mm.] and an average tip angle of 40 degrees.
Sides: Equal.
Surface: Irregularly furrowed horizontally near the apex, ridged near apex and pitted toward the base.
Ridges: Jagged toward the base.
External color: Light yellowish brown [76. l.yBr].
Internal color when cracked: Light orange yellow [70. l.OY].
Cavity surface color: Light yellowish brown [76. l.yBr] with Deep yellowish brown [75. deep yBr] blotching.
Average pit wall thickness: 1/4" [6.4 mm.].
Average width: 1 5/16" [33.3 mm.].
Average length: 1 11/16" [42.9 mm.].
Average breadth: 1" [25.4 mm.].
Tendency to split: Slight.
Kernel:
*Form.*—Oval.
*Pellicle color.*—Grayish yellow brown [80. gy.yBr].
*Skin color.*—Pale yellow [89. p.Y] when first removed.
*Vein color.*—Moderate yellow [87. m.Y] when first removed.
*Taste.*—Bitter.
*Viable.*—Yes.
*Average width.*—9/16" [14.3 mm.].
*Average length.*—13/16" [20.6 mm.].
*Amygdalin.*—Abundant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to its selected pollen parent, 'Crimson Lady' (U.S. Plant Pat. No. 7,953) peach, by producing fruit that is clingstone in type, mostly red in skin color, and yellow in flesh color, but is distinguished therefrom by requiring less chilling hours and by producing fruit that is larger in size, melting instead of in non-melting in texture, and that matures about five days later.

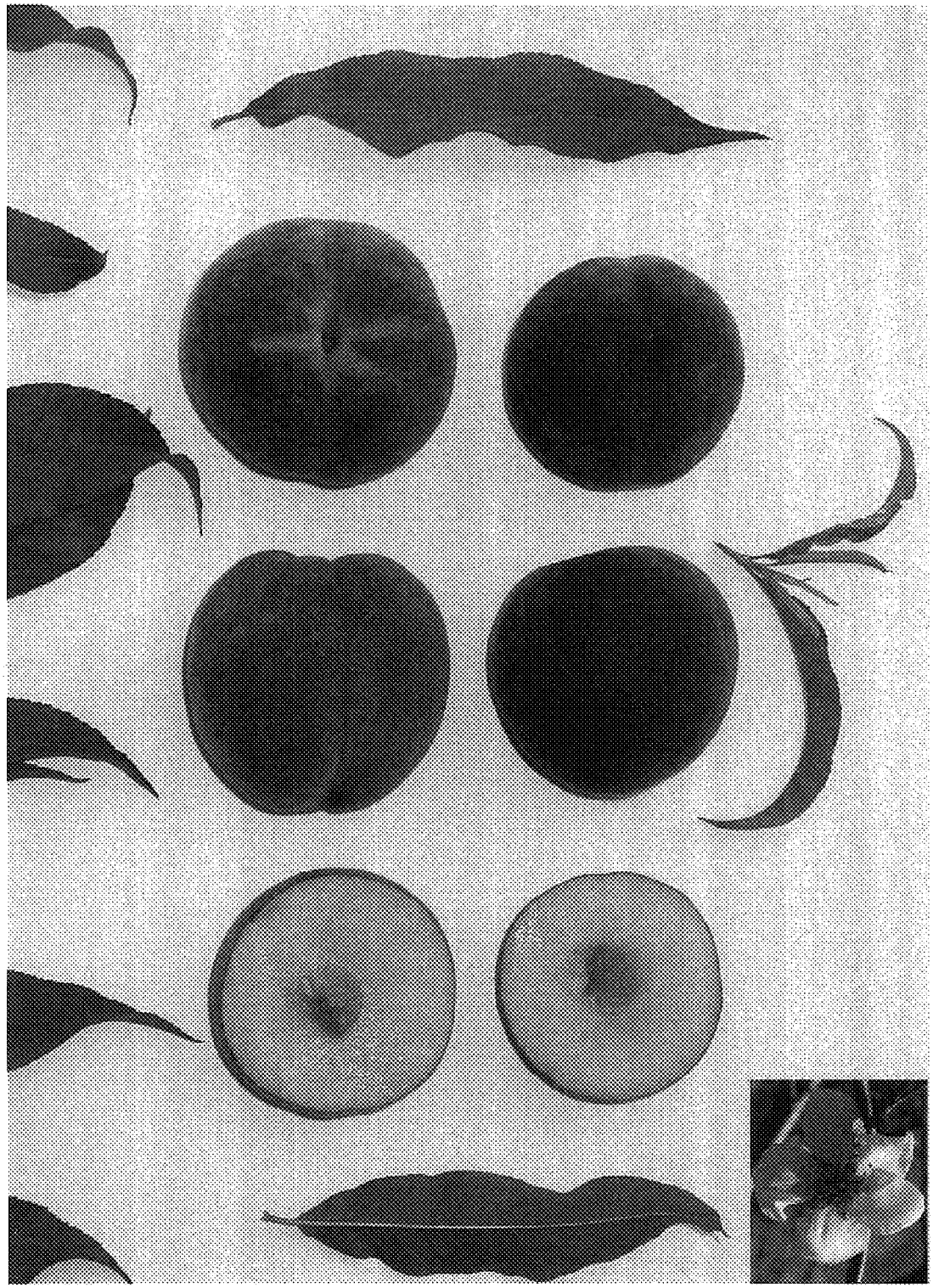

* * * * *